US008399500B2

(12) United States Patent
Erdelmeier

(10) Patent No.: US 8,399,500 B2
(45) Date of Patent: Mar. 19, 2013

(54) METHOD OF SYNTHESIZING ERGOTHIONEINE AND ANALOGS

(75) Inventor: Irene Erdelmeier, Paris (FR)

(73) Assignee: Tetrahedron, Vincennes (FR)

( * ) Notice: Subject to any disclaimer, the term of this patent is extended or adjusted under 35 U.S.C. 154(b) by 0 days.

(21) Appl. No.: 13/121,891

(22) PCT Filed: Oct. 6, 2010

(86) PCT No.: PCT/EP2010/064950
§ 371 (c)(1),
(2), (4) Date: Mar. 30, 2011

(87) PCT Pub. No.: WO2011/042480
PCT Pub. Date: Apr. 14, 2011

(65) Prior Publication Data
US 2012/0136159 A1    May 31, 2012

(30) Foreign Application Priority Data
Oct. 6, 2009 (FR) ..................... 09 56962

(51) Int. Cl.
A61K 31/417 (2006.01)
C07D 233/42 (2006.01)
(52) U.S. Cl. ..................... 514/386; 548/316.4
(58) Field of Classification Search ............... 548/316.4; 514/386
See application file for complete search history.

(56) References Cited

U.S. PATENT DOCUMENTS
2009/0093642 A1    4/2009 Trampota

FOREIGN PATENT DOCUMENTS
WO    WO 95/00494    1/1995

OTHER PUBLICATIONS

Ishikawa, Y et al. Journal Biological Chemistry, 1974, vol. 249 (14), pp. 4420-4427.*
Ishikawa, Y. et al., "Participation of an intermediate sulfoxide in the enzymatic thiolation of the imidazole ring of hercynine to form ergothioneine," The Journal of Biological Chemistry, Jul. 25, 1974, vol. 249, No. 14, pp. 4420-4427, XP002568730, ISSN: 0021-9258.
Xu, J. et al., "Synthesis of L-(+)-ergothioneine," Journal of Organic Chemistry, 1995 US, vol. 60, No. 20, 1995, pp. 6296-6301, XP002568731, ISSN: 0022-3263.
Ito, S., "Synthesis of 2-5-cysteinylhistidine and 2-mercaptohistidine via bromolactone derivative of histidine", Journal of Organic Chemistry, vol. 50, No. 19, Sep. 1985, pp. 3636-3638, XP009129621, DOI: 10.1021/jo00219a044.
Seki, M. et al., "A Novel Synthesis of (+)-Biotin from L-Cysteine", Journal of Organic Chemistry, 2002, 67, 5527-5536.
Reinhol, V. et al., "Synthesis of α-N-Methylated Histidines", J Med Chem. Mar. 1968;11(2):258-60.
Askari, A. et al., "The Reaction Sequence in Ergothioneine Biosynthesis: Hercynine Intermediate", The Journal of Biological Chemistry, vol. 237, No. 5, May 1962.
Piez, K. et al., "Desalting of Amino Acid Solutions by Ion Exchange", (from the Department of Chemistry, Northwestern University Dental School, Chicago), downloaded from www.jbc.org on Aug. 29, 2011.
Heath, H. et al., "The Synthesis of Ergothioneine", J. Chem. Soc., 1951, 2215-2217, DOI: 10.1039/JR9510002215.
Schubert, M., "Compounds of Thiol Acids with Aldehydes", J. Biol. Chem. 1936 114: 341-350.

* cited by examiner

Primary Examiner — Kamal Saeed
Assistant Examiner — Janet L Coppins
(74) Attorney, Agent, or Firm — Harness, Dickey & Pierce, P.L.C.

(57) ABSTRACT

The present disclosure relates to a method for synthesizing ergothioneine or one of the derivatives thereof of following formula (I):

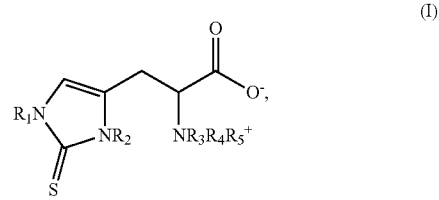

or a physiologically acceptable salt, a tautomer, a stereoisomer or a mixture of stereoisomers in all proportions thereof, from a compound of betaine type of following formula (II):

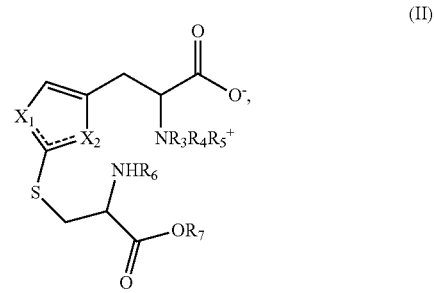

or a physiologically acceptable salt, a tautomer, a stereoisomer or a mixture of stereoisomers in all proportions thereof, by cleavage reaction in the presence of a thiol, at a temperature above or equal to 60° C.
The present disclosure also relates to compounds of formula (II) and the method of synthesis thereof.

20 Claims, No Drawings

METHOD OF SYNTHESIZING ERGOTHIONEINE AND ANALOGS

CROSS-REFERENCE TO RELATED APPLICATIONS

This application is a National Phase Entry of International Application No. PCT/EP2010/064950, filed on Oct. 6, 2010, which claims priority to French Patent Application Serial No. 0956962, filed on Oct. 6, 2009, both of which are incorporated by reference herein.

BACKGROUND AND SUMMARY

The present patent application relates to a novel method for synthesizing ergothioneine and related derivatives.

Ergothioneine, discovered in 1909 by Tanret in ergot of rye, is an amino acid of natural origin, with antioxidant properties, corresponding to the following formula:

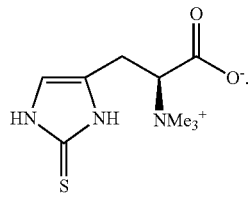

Its presence has been demonstrated not only in a large number of fungi and mycobacteria, but also in plants, animals and humans. It is at the level of their roots that plants absorb ergothioneine biosynthesized by the fungi attached thereto. It is only through their diet that higher organisms, and humans in particular, ingest this compound.

Several syntheses of this molecule have thus been proposed in the literature, but only two of them make it possible to end up with L-ergothioneine (natural enantiomer). The international application WO 95/00 494 proposes a 5-step synthesis of L-ergothioneine by reaction of the methyl ester of Nα,Nα-dimethyl-histidine (itself obtained from L-histidine in 2 steps) with phenyl chlorothioformate, then reaction with ethyl chloroformate, formation of the quaternary ammonium and finally de-protection of the sulphur and the methyl ester. Thus, such a synthesis strategy necessitates the protection of sulphur, which cannot be present in free form, in order to enable the methylation of the dimethylamine group to lead to the betaine function. In addition, the phenyl chlorothioformate must be prepared from thiophosgene ($CSCl_2$), a toxic reagent and available with difficulty in large quantity for use at the industrial scale.

The patent application US 2009/093642 also describes a 9-step synthesis of L-ergothioneine from histidine by opening of the imidazole cycle and reaction with a thiocyanate such as potassium thiocyanate, to give 2-thiohistidine (according to the method described by Heath, H. et al., 1951, J. Chem. Soc., 2215), then protection of the sulphur by a tertiobutyl group, formation of quaternary ammonium and de-protection of the sulphur. Apart from the use of large volumes of hydrochloric acid, KSCN, used in acid medium, is a highly toxic reagent.

These two methods have several common points. Apart from their high number of steps, they cumulate the drawbacks of using not only very toxic reagents but also considerable quantities of organic solvents and concentrated hydrochloric acid, which lead to risks in environmental terms. In terms of the synthesis strategy, these two methods have in common introducing sulphur, from histidine or one of the N-demethylated derivatives thereof, before generating the betaine group, which has the drawback of making the synthesis unwieldy through additional steps of protection and de-protection. Thus, there exists a real need to develop a novel method for synthesizing ergothioneine and derivatives thereof that is applicable at the industrial level, in other words which does not have difficulties of purification, which does not use products or solvents dangerous and toxic for humans and the environment, and which makes it possible to obtain, at the industrial scale, the product with a good yield and a low cost.

In aiming to develop an environmentally friendly method, at one and the same time using low toxicity reagents, minimising the number of steps and carrying out reactions in aqueous medium, the Applicant has decided to opt for a "reversed" synthesis strategy, which consists in introducing the sulphur into an intermediate already possessing the betaine group. This approach, completely original, may be considered bio-mimetic in so far as the biosynthesis by enzymatic route of L-ergothioneine in fungi proceeds in the same way (Askari, A. and Melville, D. B., 1962, J. Biol. Chem., 237, 1615-1618).

The object of the present patent application is thus a method for synthesizing a derivative of following formula (I):

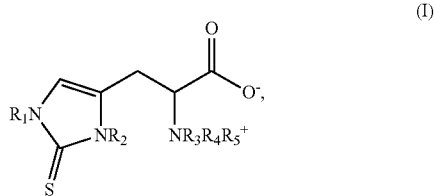

or a physiologically acceptable salt thereof, a tautomer, a stereoisomer or a mixture of stereoisomers in all proportions, in particular a mixture of enantiomers, and especially a racemic mixture thereof, for which:
  $R_1$ and $R_2$ represent, independently of each other, a hydrogen atom or a ($C_1$-$C_4$) alkyl group such as methyl, at least one of the $R_1$ and $R_2$ groups representing a hydrogen atom, and advantageously each representing a hydrogen atom, and
  $R_3$, $R_4$ and $R_5$ represent, independently of each other, a ($C_1$-$C_4$) alkyl group such as methyl,
comprising the following successive steps:
  (i) cleavage reaction of a compound of following formula (II):

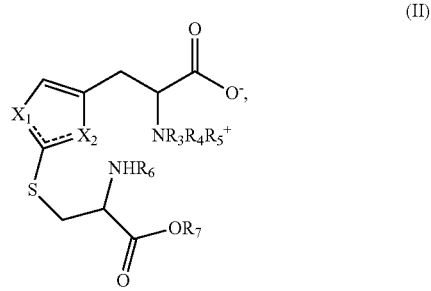

or a physiologically acceptable salt thereof, a tautomer, a stereoisomer or a mixture of stereoisomers in all proportions, in particular a mixture of enantiomers, and especially a racemic mixture thereof,
for which:

represents

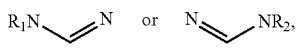

$R_1$, $R_2$, $R_3$, $R_4$ and $R_5$ are as defined above, $R_6$ represents a hydrogen atom or a ($C_1$-$C_4$) alkyl or —CO—(($C_1$-$C_4$)alkyl) group, and in particular a hydrogen atom or a —COCH$_3$ group, and more particularly a hydrogen atom, and $R_7$ represents a hydrogen atom or a ($C_1$-$C_4$) alkyl group, and in particular a hydrogen atom, in the presence of a thiol, preferably soluble in the reaction solvent which could be especially water, at a temperature above or equal to 60° C., to give a compound of formula (I), and (ii) separation of the compound of formula (I) obtained at the preceding step (i) from the reaction medium.

"Tautomer" is taken to mean, according to the present invention, a constitutional isomer of the compound obtained by prototropy, in other words by migration of a hydrogen atom and change of location of a double bond. The different tautomers of a compound are generally interconvertible and present in equilibrium, in solution, in proportions that can vary according to the solvent used, the temperature or even the pH. Within the framework of compounds of the invention, the 2-thioimidazole cycle may be present in the following different tautomer forms:

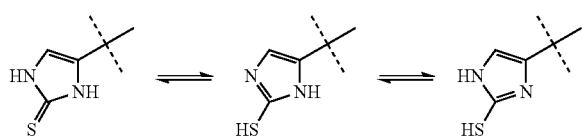

In the present invention, "physiologically acceptable" is taken to designate what is generally safe, non toxic and neither biologically nor otherwise undesirable and which is acceptable for pharmaceutical, cosmetic or food (human or animal) use, in particular food. "Physiologically acceptable salts" of a compound is taken to designate salts that are physiologically acceptable, as defined above, and which have the desired activity (pharmacological, cosmetic or food) of the parent compound. Such salts comprise:

(1) hydrates and solvates, (2) acid addition salts formed with inorganic acids such as hydrochloric acid, hydrobromic acid, sulphuric acid, nitric acid, phosphoric acid and similar; or formed with organic acids such as acetic acid, benzenesulphonic acid, benzoic acid, camphresulphonic acid, citric acid, ethanesulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and similar, or (3) the salts formed when an acid proton present in the parent compound is either replaced by a metal ion, for example an ion of alkaline metal, an ion of alkaline-earth metal or an aluminium ion; or coordinated with an organic or inorganic base. Acceptable organic bases comprise diethanolamine, ethanolamine, N-methylglucamine, triethanolamine, tromethamine and similar. Acceptable inorganic bases comprise aluminium hydroxide, calcium hydroxide, potassium hydroxide, sodium carbonate and sodium hydroxide.

"Stereoisomers" is taken to mean, according to the present invention, diastereoisomers and enantiomers. They are thus optical isomers. Stereoisomers that are not mirror images of each other are designated as "diastereoisomers", and stereoisomers that are mirror images of each other, but not superimposable, are designated as "enantiomers". A mixture containing equal quantities of two individual enantiomer forms of opposite chirality is designated as "racemic mixture".

"($C_1$-$C_4$) alkyl" group is taken to mean, according to the present invention, a saturated, linear or branched hydrocarbon chain comprising 1 to 4 atoms of carbon. It could be methyl, ethyl, propyl, isopropyl, butyl, isobutyl, sec-butyl, or tert-butyl groups. In particular, it could be the methyl group.

"Thiol" is taken to mean, according to the present invention, any reagent containing a SH group in its molecular structure. It will be more particularly a compound of formula R—SH with R representing a saturated, linear or branched, $C_1$ to $C_8$ hydrocarbon chain, especially $C_2$ to $C_6$, substituted by one or more polar substituents.

"Saturated hydrocarbon chain" is taken to mean, according to the present invention, a saturated, linear or branched hydrocarbon chain comprising advantageously 1 to 8 atoms of carbon. It could be more particularly a saturated, linear chain, such as a methyl, ethyl, propyl, butyl, pentyl or instead hexyl group.

Polar substituents are taken to mean, according to the present invention, hydrophilic groups such as OH, SH, $NH_2$ and COON groups. "Cleavage reaction" is taken to mean, according to the present invention, that the compound engaged in this reaction is split into two parts during this reaction, to make it possible in the present case to form the thiocarbonyl function of the compound of formula (I).

The compound of formula (I) could in particular be a compound of following formula (Ia):

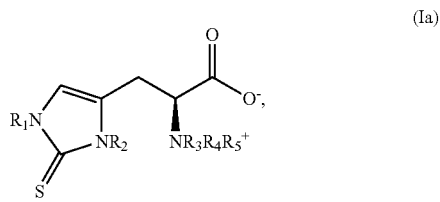

or a physiologically acceptable salt, a tautomer, a stereoisomer or a mixture of stereoisomers in all proportions, in particular a mixture of enantiomers, and especially a racemic mixture thereof, for which $R_1$, $R_2$, $R_3$, $R_4$ and $R_5$ are as defined previously.

The compound of formula (I) will represent especially ergothioneine, and in particular L-ergothioneine.

Step (i):

This cleavage reaction, carried out in the presence of a thiol, makes it possible to obtain the compound of formula (I) as well as pyruvic acid ($CH_3C(O)$—$CO_2H$) or one of the derivatives thereof, especially an ester ($CH_3C(O)$—$CO_2R_7$) or a derivative obtained by reaction with the thiol, such as a thiocetalic derivative (two molecules of thiol can react with the ketone function of the pyruvic acid). Furthermore, the thiol should preferably be soluble in the reaction solvent which could be especially water, which has the additional advantage of being more ecological. The thiol used in this step (i) could be more particularly a thiol corresponding to the formula R—SH, with R representing an alkyl chain, linear or branched, and preferably linear, comprising from 1 to 8, especially 2 to 6, in particular 2 to 4, atoms of carbon, substituted by one or more groups chosen from OH, SH, $NH_2$ and COOH.

The presence of hydrophilic groups (OH, SH, $NH_2$ and COOH) could make it possible especially to render the thiol more soluble in water, when water is used as solvent. The thiol could more particularly be chosen from cysteine, dithiothreitol, 2-mercaptoethanol, 2-mercaptopropionic acid, 3-mercaptopropionic acid and thioglycolic acid, and preferably will be 3-mercaptopropionic acid. It could also be mercaptoacetic acid and mercaptohexanoic acid.

Advantageously, at least 2 molar equivalents of thiol will be used compared to the compound (II), in other words at least 2 moles of thiol are used for one mole of compound (II) used. In particular, at least 5 molar equivalents of thiol, and especially 5 to 10 molar equivalents of thiol compared to the compound (II) could be used.

The reaction mixture is heated to a temperature above 60° C. because below this temperature the reaction kinetics would be too slow. The reaction could be carried out at a temperature ranging between 60 and 120° C., advantageously between 80 and 100° C., more particularly after addition of the thiol. The reaction could be carried out especially in acid medium.

Step (ii):

The final product obtained (compound of formula (I)) could be separated from the reaction medium by techniques well known to those skilled in the art and applicable at the industrial scale, in particular by evaporation, if appropriate partial, of solvents, followed preferably by a recrystallisation to purify the product. Since the compounds of formula (I) are soluble in water, one or more prior extractions with an organic solvent, such as for example ethyl acetate or tert-butyl-methylic ether, could make it possible to eliminate the organic by-products formed during the reaction, such as pyruvic acid or derivatives thereof, as well as the excess of thiol.

The product obtained could be purified if necessary by techniques well known to those skilled in the art, for example by recrystallisation, if appropriate after desalinisation of the aqueous phase containing it, by techniques well known to those skilled in the art (for example by electrodialysis, by addition of an adequate resin, or by reverse osmosis). Before or after this step (ii), a salt of the formed compound could be prepared, if it is so desired, especially by addition of a physiologically acceptable acid or base as defined previously.

The compound of formula (II) could be prepared from an acid addition salt, with the exclusion of the salt of hydriodic acid (HI), of a compound of betaine type of following formula (III):

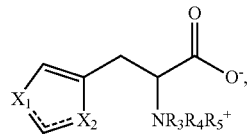

or a tautomer, a stereoisomer or a mixture of stereoisomers in all proportions, in particular a mixture of enantiomers, and especially a racemic mixture thereof, for which

$R_3$, $R_4$ and $R_5$ are as defined previously,
by reaction successively with dibromine,
then with a cysteine derivative of following formula (IV):

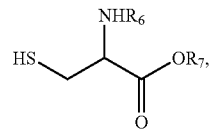

or a stereoisomer or a mixture of stereoisomers in all proportions, in particular a mixture of enantiomers, and especially a racemic mixture thereof,
in which $R_6$ and $R_7$ are as defined previously.

"Acid addition salt of the compound of betaine type of formula (III)" is taken to mean, according to the present invention, a salt of the compound of betaine type of formula (III) obtained by addition of an acid, with the exclusion of hydriodic acid HI. The acid could in particular be hydrochloric acid or sulphuric acid.

In this reaction, dibromine could be used at the rate of 1 to 1.5 molar equivalents compared to the compound of betaine type of formula (III). Preferably, the dibromine is added cold (very rapid addition preferably), at a temperature below 10° C., preferably below 5° C. The addition of dibromine could thus be carried out at a temperature ranging between −10° C. and 10° C., advantageously ranging between −5° C. and 5° C.

The cysteine derivative could in particular be N-acetylcysteine or cysteine (especially in the D, L or racemic form), and in particular cysteine and especially L-cysteine. The cysteine derivative will be advantageously used in excess, in particular at the rate of 2 to 10, advantageously 3 to 7 molar equivalents of cysteine derivative compared to the compound of betaine type of formula (III), in other words that 2 to 10, advantageously 3 to 7 moles of cysteine derivative are used for one mole of compound (III) used. This reaction could be carried out in a solvent such as water.

The yield of this step could be greater than or equal to 45%, or even greater than or equal to 60%. Preferably, the compound of formula (II) will not be isolated from the reaction medium but will be engaged directly in the following step (i). Thus, the preparation of the compound (I) from the compound (III) may be carried out in a single reactor, without isolation of the intermediate compound (II) ("one-pot").

The method for preparing a compound of formula (I) according to the invention could thus comprise the following successive steps:

(a1) reaction of an acid addition salt, with the exclusion of the salt of hydriodic acid, of a compound of betaine type of formula (III) as defined above, or a tautomer, a stereoisomer or a mixture of stereoisomers in all proportions, in particular a mixture of enantiomers, and especially a racemic mixture thereof, with dibromine, then with a cysteine derivative of formula (IV) as defined above or a stereoisomer or a mixture of stereoisomers in all proportions, in particular a mixture of enantiomers, and especially a racemic mixture thereof, and in particular with cysteine and especially L-cysteine, to give a compound of formula (II) as defined above, (b1) cleavage reaction of the compound of formula (II) obtained at the preceding step (a1) in the presence of a thiol as defined previously, preferably soluble in the reaction solvent which could be especially water, at a temperature greater than or equal to 60° C., to give a compound of formula (I), and (c1) separation of the compound of formula (I) obtained at the preceding step (b1) from the reaction medium.

The steps (b1) and (c1) correspond respectively to the preceding steps (i) and (ii). The step (a1), for its part, corresponds to the step of preparation of the compound of betaine type of formula (II) described previously. Advantageously, the steps (a1) and (b1) will be carried out in a same solvent, such as water, preferably, in a same reactor, in other words without isolation of the intermediate products (compound of formula (II) in particular).

Under these conditions, the reaction medium can contain a cysteine derivative used preferably in excess at step (a1). Before separating the compound of formula (I) from the reaction medium (step (c1)), it could thus be necessary to eliminate the excess of cysteine derivative in order to facilitate the isolation and the purification of the compound of formula (I). Especially, in the case of a cysteine derivative for which $R_7$=H or ($C_1$-$C_4$) alkyl and in particular in the case of cysteine, benzaldehyde may then be added for example, which will then form with the cysteine derivative in excess a derivative of 2-phenylthiazolidine-4-carboxylic acid, a compound which precipitates in a solvent such as water. In this way, the cysteine derivative in excess could be recycled. The overall yield of preparation of the compound of formula (I) from the compound of betaine type of formula (III) could be greater than or equal to 40%.

According to a particular embodiment of the invention, the compound of formula (I) is a compound of formula (Ia) and the method of preparation thereof comprises the following successive steps:

(a2) reaction of an acid addition salt, with the exclusion of the salt of hydriodic acid, of a compound of betaine type of following formula (IIIa):

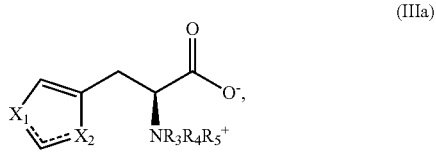

(IIIa)

or a tautomer, a stereoisomer or a mixture of stereoisomers in all proportions, in particular a mixture of enantiomers, and especially a racemic mixture thereof, for which

$R_3$, $R_4$ and $R_5$ are as defined previously, successively with dibromine, then with a cysteine derivative of formula (IV) as defined above or a stereoisomer or a mixture of stereoisomers in all proportions, in particular a mixture of enantiomers, and especially a racemic mixture thereof, and in particular with cysteine and especially L-cysteine, to give a compound of betaine type of following formula (IIa):

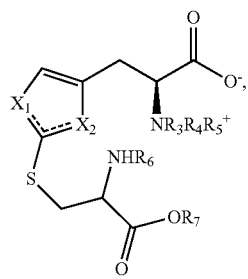

(IIa)

or a physiologically acceptable salt, a tautomer, a stereoisomer or a mixture of stereoisomers in all proportions, in particular a mixture of enantiomers, and especially a racemic mixture thereof, for which

$R_3$, $R_4$, $R_5$, $R_6$ and $R_7$ are as defined previously, (b2) cleavage reaction of the compound of betaine type of formula (IIa) obtained at the preceding step (a2) in the presence of a thiol as defined previously, preferably soluble in the reaction solvent which could be especially water, and in particular with cysteine, dithiothreitol, 2-mercaptoethanol, 2-mercaptopropionic acid, 3-mercaptopropionic acid or thioglycolic acid, and preferably with 3-mercaptopropionic acid, at a temperature above or equal to 60° C., to give a compound of formula (Ia), and (c2) separation of the compound of formula (Ia) obtained at the preceding step (b2) from the reaction medium.

The steps (a2), (b2) and (c2) correspond respectively to the preceding steps (a1), (b1) and (c1). The compounds of formula (IIa) represent particular forms of the compound of formula (II). Similarly, the compounds of betaine type of formula (IIIa) represent particular forms of the compound of betaine type of formula (III).

Another object of the present invention is a compound of following formula (II):

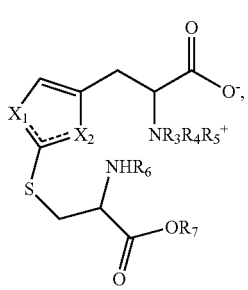

(II)

or a physiologically acceptable salt, a tautomer, a stereoisomer or a mixture of stereoisomers in all proportions, in particular a mixture of enantiomers, and especially a racemic mixture thereof,
for which:

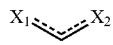

represents

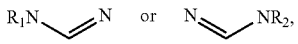

and
$R_1$, $R_2$, $R_3$, $R_4$, $R_5$, $R_6$ and $R_7$ are as defined previously, with the exclusion of the compound for which

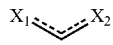

represents

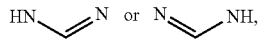

$R_3$, $R_4$ and $R_5$ each represent a methyl group and $R_6$ and $R_7$ each represent a hydrogen atom.

The excluded compound is described in: Ishikawa et al. *J. Biol. Chem.* 1974, 249(14), 4420. In particular, it will not be a compound of formula (II) for which

represents

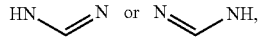

and $R_3$, $R_4$ and $R_5$ each represent a methyl group. It could be especially a compound of formula (IIa) as defined previously. In particular, this compound could be 2-{2-[(2-ammonio-2-carboxyethyl)thio]-1H-imidazol-4-yl}-1-carboxy-N,N,N-trimethylethanaminium dihydrochloride (Herc-Cys, 2HCl).

Another object of the present invention is a method for preparing a compound of following formula (II):

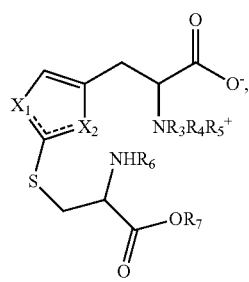

(II)

or a physiologically acceptable salt, a tautomer, a stereoisomer or a mixture of stereoisomers in all proportions, in particular a mixture of enantiomers, and especially a racemic mixture thereof,
for which:

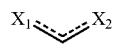

represents

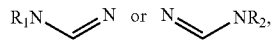

and
$R_1$, $R_2$, $R_3$, $R_4$, $R_5$, $R_6$ and $R_7$ are as defined previously, by reaction of an acid addition salt, with the exclusion of the salt of hydriodic acid, of a compound of betaine type of formula (III) as defined previously, or a tautomer, a stereoisomer or a mixture of stereoisomers in all proportions, in particular a mixture of enantiomers, and especially a racemic mixture thereof, for which

$R_3$, $R_4$ and $R_5$ are as defined previously, successively with dibromine, then with a cysteine derivative of formula (IV) as defined previously.

In this reaction, dibromine could be used at the rate of 1 to 1.5 molar equivalents compared to the compound of betaine type of formula (III). Preferably, the dibromine is added cold (very rapid addition preferably), at a temperature below 10° C., preferably below 5° C. The addition of the dibromine could thus be carried out at a temperature ranging between −10° C. and 10° C., advantageously ranging between −5° C. and 5° C.

The cysteine derivative could in particular be N-acetylcysteine or cysteine (especially in the D, L or racemic form), and in particular cysteine and especially L-cysteine. The cysteine derivative will be advantageously used in excess, in particular at the rate of 2 to 10, advantageously 3 to 7 molar equivalents of cysteine derivative compared to the compound of betaine type of formula (III), in other words 2 to 10, advantageously 3 to 7 moles of cysteine derivative are used for one mole of compound (III) used. This reaction could be carried out in a solvent such as water.

DETAILED DESCRIPTION

The present invention will be better understood in the light of the examples that follow, which are given simply by way of illustration and in no way limit the scope of the invention.

EXAMPLES

All of the reactions are carried out in the open air unless otherwise indicated.

1—Preparation of Compounds of Formula (II) According to the Invention

Example 1

Preparation of 2-{2-[(2-ammonio-2-carboxyethyl)thio]-1H-imidazol-4-yl}-1-carboxy-N,N,N-trimethylethanaminium dihydrochloride (Herc-Cys, 2HC1)

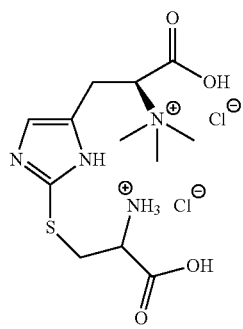 [SMILES: C[N+](C)(C)[C@@H](Cc1cnc(SCC([NH3+])C(=O)O)[nH]1)C(=O)O ; [Cl-] ; [Cl-]]

986 mg (5 mmoles) of Hercynine (V. N. Reinhold et al., *J. Med. Chem.* 11, 258 (1968)) are dissolved in 10 mL of water. 417 μL (5 mmoles) of concentrated hydrochloric acid is added, then the solution is cooled to 0° C. Under very strong stirring, 308 μL (959 mg, 6 mmoles, 1.2 equiv.) of dibromine are added drop by drop (addition time 1 min 20). The reaction mixture turns yellow and a reddish solid is formed. Five minutes after the end of the addition of the dibromine, 1.87 g (15 mmoles, 3 equiv.) of L-Cysteine are added. Immediately, the mixture loses its colour, and the reddish precipitate dissolves in several minutes.

After stirring at 0° C. for 1 h, the mixture is filtered, and the precipitate washed with 2×0.5 mL of water. The filtrate is deposited on a column filled with 75 g of DOWEX® 50WX2-400, conditioned beforehand with 1N hydrochloric acid HC1. After elution with 400 mL of 1N hydrochloric acid HC1, then 500 mL of 2N hydrochloric acid HC1, the fractions containing the desired product are recombined. After evaporation and 2 co-evaporations with 2×20 mL of toluene, after drying 894 mg (46%) of the desired product are obtained in the form of yellow crystals. (This product has been synthesised with a low yield from ergothioneine and Chloroalanine, but in the form of free amino acid, by Ishikawa et al., *J. Biol. Chem.* 249 (14), 4420 (1974).)

$^1$H-NMR (D$_2$O/DC1, 400 MHz): δ (ppm)=3.14 (s, 9H); 3.37 (m, 2H); 3.56 (m, 2H); 4.20 (m, 1H); 4.28 (m, 1H); 7.31 (s, 1H).

UPLC-MS (ES+): 317.4 (MH+)

Example 2

Preparation of 2-{2-[(2-ammonio-2-carboxyethyl)thio]-1H-imidazol-4-yl}-1-carboxy-N,N,N-trimethylethanaminium dichloride dihydrochloride (Herc-Cys, 2HC1)—variation of the quantity of L-Cysteine

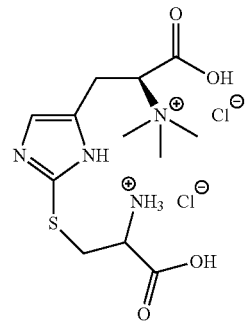 [SMILES: C[N+](C)(C)[C@@H](Cc1cnc(SCC([NH3+])C(=O)O)[nH]1)C(=O)O ; [Cl-] ; [Cl-]]

The same method as described in Example 1 is used, except that 3.12 g (25 mmoles, 5 equiv.) of L-Cysteine are added, seven minutes after the end of the addition of dibromine. After treatment and purification on a DOWEX® column, 1.13 g (58%) of the desired product are obtained after drying in the form of yellow crystals. The $^1$H-NMR (D$_2$O/DC1) analysis is identical to that described in Example 1.

2—Preparation of Compounds of Formula (I) According to the Invention from Intermediates of Formula (II)

Example 3

Preparation of L-Ergothioneine by Cleavage of Herc-Cys, 2HC1

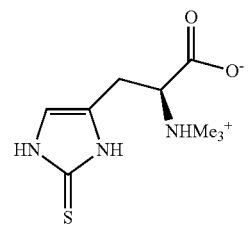

1.67 g (4.4 mmoles) of Herc-Cys, 2HC1 are solubilised in 16.7 mL of water, and 1.895 mL (2.29 g, 21.39 mmoles, 5 equiv.) of 3-mercaptopropionic acid are added. The clear, slightly yellow mixture is heated under stirring for 24 h at 85° C. Then 1.895 mL (2.29 g, 21.39 mmoles, 5 equiv.) of 3-mercaptopropionic acid is again added, and the heating is continued for 48 h.

The reaction mixture is cooled to 0° C., and a white precipitate forms. After filtration and rinsing of the precipitate with 2×2 mL of cold water, the filtrate is washed with 5×20 mL of dichloromethane and 5×20 mL of ethyl acetate.

The aqueous phase is evaporated under vacuum, and the residue dissolved in 33 mL of water. By addition of a 20% ammonia solution, the pH of the solution is adjusted to 6. After lyophilisation, the powder obtained is hot solubilised in an ethanol/water mixture (7/1). After addition of activated charcoal (100 mg) and hot filtration on Clarcel, the solution obtained is maintained cold for 14 h. After filtration and drying, 676 mg (69%) of L-Ergothioneine is obtained in the form of a white powder. The analytical data obtained are identical to those obtained in the literature (J. Xu, J. C. Yadan, *J. Org. Chem.* 60, 6296-6301 (1995)).

$^1$H-NMR (D$_2$O, 400 MHz): δ (ppm)=3.20 (m, 2H); 3.29 (s, 9H); 3.90 (dd, J=11 Hz, J=5 Hz, 1H), 6.81 (s, 1H).

UPLC-MS (ES+): 230.6 (MH+)

3—Preparation of Compounds of Formula (I) According to the Invention without Isolation of Intermediates of Formula (II)

Example 4

One pot preparation of L-Ergothioneine from Hercynine—Purification after Desalinisation of the Aqueous Phase with a Resin a) Formation of the Adduct Herc-Cys (Compound of Formula (II))

19.72 g (0.1 mole) of Hercynine (V. N. Reinhold et al., *J. Med. Chem.* 11, 258 (1968)) are dissolved in 200 mL of water. 8.35 mL (0.1 mole) of concentrated hydrochloric acid are added, then the solution is cooled to 2° C. Under very strong stirring, 6.68 mL (20.77 g, 130 mmoles, 1.3 equiv.) of dibromine are added drop by drop without exceeding 3° C. (addition time 10 min). The reaction mixture turns yellow and a reddish solid is formed. Seven minutes after the end of the addition of the dibromine, 62.4 g (0.5 moles, 5 equiv.) of L-Cysteine are added, and the internal temperature rises to 3° C. Immediately, the mixture loses it colour, and the reddish precipitate dissolves in several minutes.

After stirring at 0° C. for 1 h, an analysis of a sample by $^1$H-NMR (D$_2$O) shows that the adduct Herc-Cys is formed with a reaction yield of 55%. The ice bath is removed, and the reaction mixture is left to stir for one hour. The internal temperature rises to 10° C. The product obtained is not isolated from the reaction medium and is used directly in the following step.

b) Formation of L-Ergothioneine

Then, 87.7 mL (106 g, 10 equiv.) of 3-mercaptopropionic acid are added to the mixture, and it is heated under strong stirring at 80° C. for 22 h. An analysis of a sample by $^1$H-NMR (D$_2$O) shows that the adduct Herc-Cys is completely cleaved into Ergothioneine.

c) Isolation of L-Ergothioneine

After cooling to room temperature, the orange-brown coloured mixture is extracted with 4×400 mL of ethyl acetate. The aqueous phase is retained, and the pH is adjusted to 4.5-5 with a 20% aqueous ammonia solution (around 21 mL). In order to trap the excess of L-cysteine present in the medium, 50.8 mL (53.0 g, 5 equiv.) of benzaldehyde is added (according to M. P. Schubert, *J. Biol. Chem.* 114, 341-350 (1936) or M. Seki et al., *J. Org. Chem.* 67 (16), 5532 (2002)).

The mixture is stirred at room temperature for 15 h, and 2-phenylthiazolidine-4-carboxylic acid precipitates in the form of a light yellow solid. After filtration of the solid and rinsing with 4×50 mL of water, the filtrate is extracted with 2×200 mL of ethyl acetate.

d) Purification after Desalinisation of the Aqueous Phase with a Resin

To facilitate the crystallisation of the final product, the aqueous phase retained is desalinised. To do this, it is treated for example with Amberlite IRA 410 resin in the form of hydrogencarbonate (according to K. A. Piez et al., *J. Biol. Chem.* 194, 669-672 (1952)). 120 g of the resin are added to the reaction mixture and it is stirred for 2 h at room temperature. A strong release of gas is observed, as well as a progressive discoloration of the medium. Moreover, the pH of the reaction mixture drops to pH=8. After 2 h of contact time, the resin is filtered. After rinsing with 5×20 mL of water, the operation is repeated again twice.

The filtrate is then evaporated to dryness, and the solid obtained is recrystallised with aqueous ethanol. 8.21 g (34.9%) of L-Ergothioneine are obtained in the form of a white powder.

$^1$H-NMR (D$_2$O, 400 MHz): δ (ppm)=3.20 (m, 2H); 3.29 (s, 9H); 3.90 (dd, J=11 Hz, J=5 Hz, 1H); 6.81 (s, 1H).

UPLC-MS (ES+): 230.6 (MH+)

$[α]_D$=+124.6°(c=1,H$_2$O)

Example 5

"One-Pot" Preparation of L-Ergothioneine from Hercynine—Purification after Desalinisation of the Aqueous Phase by Electrodialysis a) Formation of the Adduct Herc-Cys (Compound of Formula (II))

98.6 g (0.5 mole) of Hercynine are dissolved in 1.5 L of water. The solution is transferred to a glass double jacketed reactor with mechanical stirring. 41.75 mL (0.5 mole) of concentrated hydrochloric acid is added, then the solution is cooled to 0° C. Under very strong stirring, 34 mL (106 g, 0.66 mole, 1.3 equiv.) of dibromine are added drop by drop without exceeding 2° C. (addition time 6.5 min). The reaction mixture turns yellow, and reddish flakes are formed. Seven minutes after the end of the addition of the dibromine, 432 g (3.5 moles, 7 equiv.) of L-Cysteine are added, and the internal temperature rises to 4° C. Immediately, the mixture loses its colour, and the reddish precipitate dissolves in several minutes. A whitish suspension is obtained.

After stirring at 0° C. for 1 h, an analysis of a sample by $^1$H-NMR (D$_2$O) shows that the adduct Herc-Cys is formed with a reaction yield of 56%. The cooling system is stopped, and the reaction mixture is left to stir for one hour. The internal temperature rises to 10° C.

b) Formation of L-Ergothioneine

Then, 441 mL (533 g, 5 moles, 10 equiv.) of 3-mercaptopropionic acid are added to the mixture, and it is heated under strong stirring at 80° C. for 24 h.

An analysis of a sample by $^1$H-NMR (D$_2$O) shows that the adduct Herc-Cys is completely cleaved into Ergothioneine.

c) Isolation of L-Ergothioneine

After cooling to room temperature, the mixture of an orange-brown colour is extracted with 4×2 L of ethyl acetate. The aqueous phase is retained, and the pH is adjusted to 4.5-5 with a 20% aqueous ammonia solution (around 110 mL). In order to trap the excess of cysteine present in the medium, 359 mL (375 g, 3.5 moles, 7 equiv.) of benzaldehyde are added (according to M. P. Schubert, *J. Biol. Chem.* 114, 341-350 (1936) or M. Seki et al., *J. Org. Chem.* 67 (16), 5532 (2002)).

The mixture is stirred at room temperature for 15 h, and 2-phenylthiazolidine-4-carboxylic acid precipitates in the form of a light yellow solid. After filtration of the solid and rinsing with 4×500 mL of water, the filtrate is extracted with 4×1.5 L of ethyl acetate.

d) Purification after Desalinisation of the Aqueous Phase by Electrodialysis

To facilitate the crystallisation of the final product, the aqueous phase retained is desalinised. To do this, it is for example desalinised by electrodialysis (Bench Scale Electrodialysis Pump System BED 1-3 of PCCell (Germany), cell ED200-020, 20 pairs of membranes (cation exchange PC-SK, anion-exchange PC-SA), 10V). The desalinised solution is then evaporated to dryness, and the solid obtained is recrystallised with aqueous ethanol. 47.68 g (41%) of L-Ergothioneine are obtained in the form of a white powder.

$^1$H-NMR (D$_2$O, 400 MHz): δ (ppm)=3.20 (m, 2H); 3.29 (s, 9H); 3.90 (dd, J=11 Hz, J=5 Hz, 1H); 6.81 (s, 1H).

UPLC-MS (ES-F: 230.6 (MH+)

$[α]_D$=+125.2°(c=1,H$_2$O)

The invention claimed is:

1. A method for synthesizing a derivative of following formula (I):

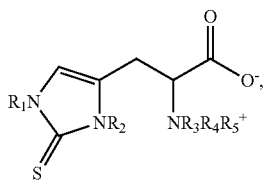

(I)

or a physiologically acceptable salt thereof, a tautomer, a stereoisomer or a mixture of stereoisomers in all proportions;

for which:
 $R_1$ and $R_2$ represent, independently of each other, a hydrogen atom or a ($C_1$-$C_4$) alkyl group, at least one of the $R_1$ and $R_2$ groups representing a hydrogen atom; and
 $R_3$, $R_4$ and $R_5$ represent, independently of each other, a ($C_1$-$C_4$) alkyl group;

comprising the following successive steps:
 (i) cleavage reaction of a compound of betaine type of following formula (II):

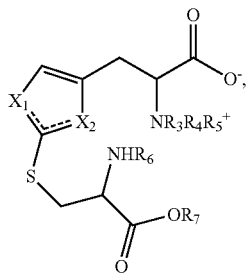

(II)

or a physiologically acceptable salt, a tautomer, a stereoisomer or a mixture of stereoisomers in all proportions;

for which:

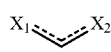

represents

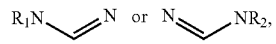

$R_1$, $R_2$, $R_3$, $R_4$ and $R_5$ are as defined above,
$R_6$ represents a hydrogen atom or a ($C_1$-$C_4$) alkyl or —CO—(($C_1$-$C_4$)alkyl) group, and
$R_7$ represents a hydrogen atom or a ($C_1$-$C_4$) alkyl group;
in the presence of a thiol, at a temperature above or equal to 60° C., to give a compound of formula (I); and
 (ii) separation of the compound of formula (I) obtained at the preceding step (i) from the reaction medium.

2. The method according to claim 1, wherein the thiol corresponds to the formula R—SH, with R representing a linear or branched alkyl chain, comprising from 1 to 8, atoms of carbon, substituted by one or more groups chosen from OH, SH, NH$_2$ and COOH.

3. The method according to claim 2, wherein the thiol is chosen from cysteine, dithiothreitol, 2-mercaptoethanol, 2-mercaptopropionic acid, 3-mercaptopropionic acid, mercaptoacetic acid, mercaptohexanoic acid and thioglycolic acid.

4. The method according to claim 1, wherein the step (i) is carried out at a temperature ranging between 60 and 120° C.

5. The method according to claim 1, wherein the compound of formula (I) corresponds to the following formula (Ia):

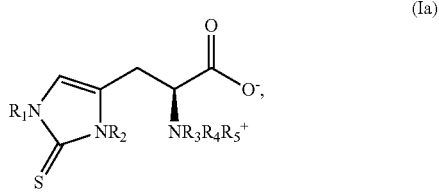

(Ia)

or to a physiologically acceptable salt thereof, a tautomer, a stereoisomer or a mixture of stereoisomers in all proportions, for which $R_1$, $R_2$, $R_3$, $R_4$ and $R_5$ are as defined in claim 1.

6. The method according to claim 1, wherein the compound of formula (I) represents ergothioneine.

7. The method according to claim 1, wherein the compound of betaine type of formula (II) is prepared from an acid addition salt, with the exclusion of the salt of hydriodic acid, of a compound of betaine type of following formula (III):

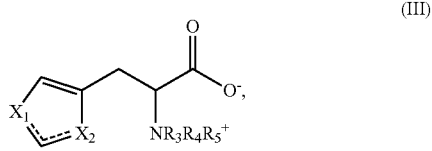

(III)

or a tautomer, a stereoisomer or a mixture of stereoisomers in all proportions;

for which

$R_3$, $R_4$ and $R_5$ are as defined in claim 1, by reaction successively with dibromine;

then with a cysteine derivative of following formula (IV):

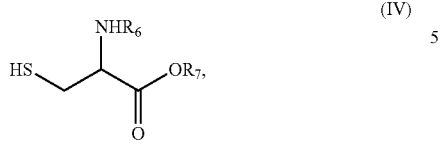

or a stereoisomer or a mixture of stereoisomers in all proportions;
in which $R_6$ and $R_7$ are as defined in claim 1.

8. The method according to claim 7, wherein the compound of formula (I) corresponds to the formula (Ia) and the method comprises the following successive steps:
(a2) reaction of an acid addition salt, with the exclusion of the salt of hydriodic acid, of a compound of betaine type of following formula (IIIa):

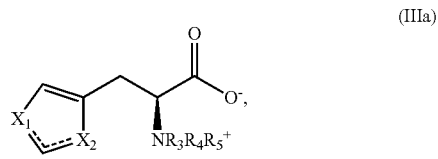

or a tautomer, a stereoisomer or a mixture of stereoisomers in all proportions;
for which

$R_3$, $R_4$ and $R_5$ are as defined in claim 7,
successively with dibromine;
then with a cysteine derivative of formula (IV) as defined in claim 7 or a stereoisomer or a mixture of stereoisomers in all proportions, to give a compound of betaine type of following formula (IIa):

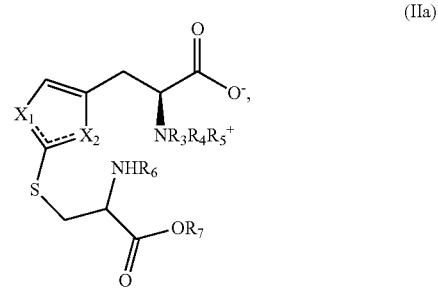

or a physiologically acceptable salt, a tautomer, a stereoisomer or a mixture of stereoisomers in all proportions; for which

$R_3$, $R_4$, $R_5$, $R_6$ and $R_7$ are as defined in claim 7,
(b2) cleavage reaction of the compound of betaine type of formula (IIa) obtained at the preceding step (a2) in the presence of a thiol, at a temperature above or equal to 60° C., to give a compound of formula (Ia); and
(c2) separation of the compound of formula (Ia) obtained at the preceding step (b2) from the reaction medium.

9. The method according to claim 7, wherein the cysteine derivative is used in excess, at the rate of 2 to 10 molar equivalent; of cysteine derivative compared to the compound of betaine type of formula (III).

10. The method according to claim 7, wherein dibromine is used at the rate of 1 to 1.5 molar equivalents compared to the compound of betaine type of formula (III).

11. The method according to claim 7, wherein the preparation of the compound (I) from the compound (III) is carried out in a single reactor, without isolation of the intermediate compound (II).

12. A compound of betaine type of following formula (II):

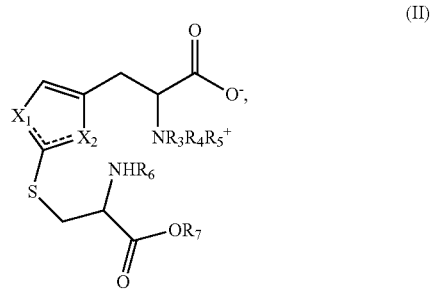

or a physiologically acceptable salt, a tautomer, a stereoisomer or a mixture of stereoisomers in all proportions;
for which:

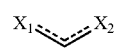

represents

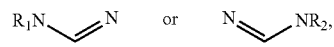

and
$R_1$, $R_2$, $R_3$, $R_4$, $R_5$, $R_6$ and $R_7$ are as defined in claim 1;
with the exclusion of the compound for which

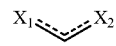

represents

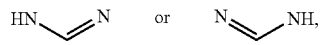

$R_3$, $R_4$ and $R_5$ each represent a methyl group and $R_6$ and $R_7$ each represent a hydrogen atom.

13. A method for preparing a compound of betaine type of following formula (II):

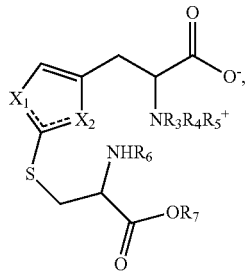

or a physiologically acceptable salt, a tautomer, a stereoisomer or a mixture of stereoisomers in all proportions; for which:

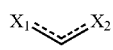

represents

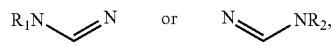

and $R_1$, $R_2$, $R_3$, $R_4$, $R_5$, $R_6$ and $R_7$ are as defined in claim 1;

by reaction of an acid addition salt, with the exclusion of the salt of hydriodic acid, of a compound of betaine type of formula (III), with dibromine, then with a cysteine derivative of formula (IV).

14. The method according to claim 13, wherein the dibromine is used at the rate of 1 to 1.5 molar equivalents compared to the compound of betaine type of formula (III).

15. The method according to claim 13, wherein the cysteine derivative is used in excess, at the rate of 2 to 10 molar equivalents of cysteine derivative compared to the compound of betaine type of formula (III).

16. The method according to claim 1 wherein the mixture of stereoisomers is a racemic mixture.

17. The method according to claim 1 wherein $R_1$ and $R_2$ represent a hydrogen atom.

18. The method according to claim 1 wherein said thiol is soluble in the reaction solvent which is water.

19. The method according to claim 6 wherein the compound of formula (I) represents L-ergothioneine.

20. The method according to claim 13 wherein said cysteine derivative is L-cysteine.

* * * * *